US012629321B2

(12) United States Patent
Huber et al.

(10) Patent No.: US 12,629,321 B2
(45) Date of Patent: May 19, 2026

(54) COMPOSITIONS AND RELATED METHODS

(71) Applicant: Colgate-Palmolive Company, New York, NY (US)

(72) Inventors: Norbert Huber, Basel (CH); Turan Matur, Binningen (CH); Ruth Hinrichs, Therwil (CH); Jeannine Loetscher, Ettingen (CH)

(73) Assignee: Colgate-Palmolive Company, New York, NY (US)

( * ) Notice: Subject to any disclaimer, the term of this patent is extended or adjusted under 35 U.S.C. 154(b) by 730 days.

(21) Appl. No.: 17/632,182

(22) PCT Filed: Dec. 17, 2021

(86) PCT No.: PCT/US2021/064066
§ 371 (c)(1),
(2) Date: Feb. 1, 2022

(87) PCT Pub. No.: WO2022/133234
PCT Pub. Date: Jun. 23, 2022

(65) Prior Publication Data
US 2023/0355487 A1       Nov. 9, 2023

Related U.S. Application Data

(60) Provisional application No. 63/127,791, filed on Dec. 18, 2020.

(51) Int. Cl.
| | |
|---|---|
| *A61K 8/21* | (2006.01) |
| *A61K 8/20* | (2006.01) |
| *A61K 8/25* | (2006.01) |
| *A61K 8/27* | (2006.01) |
| *A61K 8/34* | (2006.01) |
| *A61K 8/41* | (2006.01) |
| *A61K 8/81* | (2006.01) |
| *A61Q 11/00* | (2006.01) |

(52) U.S. Cl.
CPC .................. *A61K 8/21* (2013.01); *A61K 8/20* (2013.01); *A61K 8/27* (2013.01); *A61K 8/41* (2013.01); *A61K 8/8176* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 4,522,806 A | 6/1985 | Muhlemann et al. | |
| 6,417,207 B1 | 7/2002 | Garvey et al. | |
| 10,342,750 B2 | 7/2019 | Prencipe et al. | |
| 2012/0288548 A1* | 11/2012 | Boyd .................... | A61K 8/731 424/49 |
| 2013/0209375 A1* | 8/2013 | Moya Argilagos .... | A61K 8/416 424/52 |
| 2017/0367948 A1 | 12/2017 | Thomson et al. | |
| 2018/0021234 A1 | 1/2018 | Prencipe et al. | |
| 2019/0269586 A1 | 9/2019 | Prencipe et al. | |
| 2020/0197271 A1 | 6/2020 | Manus et al. | |

FOREIGN PATENT DOCUMENTS

| | | | | |
|---|---|---|---|---|
| CN | 102159083 | 8/2011 | | |
| CN | 102656142 | 9/2012 | | |
| CN | 108078798 | 5/2018 | | |
| CN | 110099721 | 8/2019 | | |
| SG | 165839 | 11/2010 | | |
| WO | 2001/039737 | 6/2001 | | |
| WO | 2009/130319 | 10/2009 | | |
| WO | WO-2010112577 A1 * | 10/2010 | ............. | A61K 31/05 |
| WO | 2014/088572 | 6/2014 | | |
| WO | 2014/094900 | 6/2014 | | |
| WO | WO-2017116444 A1 * | 7/2017 | ............. | A01N 31/02 |
| WO | 2017/223497 | 12/2017 | | |

OTHER PUBLICATIONS

Hampelska et al ("The Role of Oral Microbiota in Intra-Oral Halitosis", Journal of Clinical Medicine, vol. 9(8), Aug. 2020), an article obtained at the website: https://pubmed.ncbi.nlm.nih.gov/32748883/) (Year: 2020).*
International Search Report and the Written Opinion of the International Searching Authority issued in International Application PCT/US2021/064066 mailed Apr. 7, 2022.

* cited by examiner

*Primary Examiner* — Sin J Lee

(57) ABSTRACT

The present disclosure relates to storage-stable compositions comprising amines and zinc-containing compounds. Related methods of use and making are further disclosed.

2 Claims, No Drawings

COMPOSITIONS AND RELATED METHODS

FIELD

The present disclosure relates to compositions containing amines and zinc-containing compounds, as well as related methods for use of said compositions.

BACKGROUND

It is known that oral hygiene compositions, by their cleaning action, make a contribution to the hygiene of the oral cavity and thus to the preservation of the health of teeth and gums. The cleaning action of these oral hygiene compositions is customarily supplemented by admixture of active compounds which prevent or control pathological symptoms in the oral cavity, in particular also the formation of bacterial films on the teeth (i.e., plaque).

These films consist of polysaccharides, primarily of dextrans. In addition to the low-molecular weight sugars, these polysaccharides form a source of nutrition for the plaque bacteria, which are mainly streptococci and lactobacillaceae. The plaque bacteria gradually break down the polysaccharides to form acidic degradation products (e.g., pyruvic acid, lactic acid, etc.). The pH decrease resulting therefrom brings about the degradation of the tooth enamel known as caries. This condition may lead to further complications, such as gingivitis and/or periodontitis.

It has therefore already been attempted to take steps against the formation of pathological symptoms in the oral cavity using various oral hygiene compositions (e.g., toothpastes, rinsing solutions or dental gels). Active compounds already known the prior art include N-octadeca-9-enylamine hydrofluoride (international non-proprietary name "dectaflur") and N'-octadecyl-N',N,N-tris(2-hydroxyethyl)-1,3-propanediamine dihydrofluoride (international non-proprietary name "olaflur"). On oral use of the hygiene composition, these active compounds form a thin hydrophobic film on the tooth enamel, the amine hydrofluoride groups coming into contact with the tooth enamel. Thus, on the one hand the tooth enamel becomes more resistant to acid attacks on account of the CaF2 covering layer formed, on the other hand the long-chain hydrocarbon residues form a hydrophobic layer which prevents the formation of deposits and the attack of the acidic degradation products on the tooth enamel.

Zinc is also a known antimicrobial agent used in oral care compositions like toothpastes or mouthrinses. Zinc is a known essential mineral for human health, and has been reported to help strengthen dental enamel and to promote cell repair. Unfortunately, conventional toothpaste formulations often require high concentrations of zinc, e.g., 2% by weight or more, to achieve efficacy. At this concentration, the zinc imparts a notably astringent taste to the composition. There is thus a need for improved antibacterial toothpaste formulations that do not suffer from the drawbacks of conventional compositions.

Accordingly, in view of the drawbacks and disadvantages to using various antimicrobials, such as zinc, there is a need for oral care compositions with anti-bacterial efficacy, but which are also palatable and desirable for a user.

BRIEF SUMMARY

Provided herein are methods of in situ synthesis of amine fluorides from amine bases without the use of hydrofluoric acid. Related compositions (e.g., oral care compositions and/or personal care compositions) are also disclosed.

Thus, in a first aspect, the present disclosure is directed to an oral care composition comprising:
an amine base,
a fluoride source,
and a zinc source selected from zinc lactate and zinc citrate.

DETAILED DESCRIPTION

As used herein, the term "oral care composition" means the total composition that is delivered to the oral surfaces. The composition is further defined as a product which, during the normal course of usage, is not, the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, sprays, toothpaste powders, tablets, and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively, the oral composition may be dual phase dispensed from a separated compartment dispenser.

As used herein, the term "amine base" may refer to a primary amine base, a secondary amine base or a tertiary amine base. "Primary amine base" refers to a compound containing at least one amine in which the nitrogen atom is directly bonded to one carbon of any hybridization, except for carbonyl group carbons. "Secondary amine base" refers to a compound containing at least one amine in which the nitrogen atom is directly bonded to two carbons of any hybridization, except for carbonyl group carbons. "Tertiary amine base" refers to a compound containing at least one amine in which the nitrogen atom is directly bonded to three carbons of any hybridization, except for carbonyl group carbons. "Amine base" may be used to refer to compounds containing a plurality of primary, secondary and/or tertiary amine groups (e.g., a tertiary polyamine). In particular, the term "amine base" excludes acid addition salts (e.g., hydrochloride salts and hydrofluoride salts), and thus refers to the free base form of the molecule. Hydrofluoride derivatives of amines are referred to herein as "amine fluorides." In methods for the production or manufacture of a composition containing an amine fluoride, an amine base may be a precursor to forming the amine fluoride.

As used herein, the term "in situ" is used to refer to the formation of a chemical product (e.g., amine fluoride) in the oral care composition or the personal care composition. For example, the reaction may be a salination reaction carried out by mixing an amine with a fluoride source and an acid, thus creating an amine fluoride and a salt. In some embodiments, in situ excludes the possibility of formation of the reaction product in a first reaction vessel (for example, at a first location), and subsequent addition of the reaction product to a mixture, admixture, or solution in a second vessel (for example, at a second location) containing other ingredients of the oral care composition or personal care composition.

Compositions of the Present Disclosure

In another aspect, the disclosure is directed to an oral care composition (Composition 1) comprising an amine base, a fluoride source, and a zinc source selected from zinc lactate and zinc citrate.

For example, the present disclosure contemplates any of the following compositions (unless otherwise indicated, values are given as percentage of the overall weight of the composition):

1.1 Composition 1, wherein the amine base is a primary amine, secondary amine, tertiary amine or a combination thereof.

1.2 Any of the preceding compositions, wherein the amine base comprises or consists of a primary amine base.

1.3 Any of the preceding compositions, wherein the amine base comprises or consists of a secondary amine base.

1.4 Any of the preceding compositions, wherein the amine base comprises or consists of a tertiary amine base.

1.5 Any of the preceding compositions, wherein the amine base is plant-derived.

1.6 Any of the preceding methods, wherein the amine base is animal-derived.

1.7 Any of the preceding methods, wherein the amine base is derived from bovine tallow.

1.8 Any of the preceding compositions, wherein the amine base is derived from rapeseed oil or from rice bran oil.

1.9 Any of the preceding compositions, wherein the amine base is a linear or branched fatty amine or polyamine, or mixtures thereof.

1.10 The preceding composition, wherein the amine base is a saturated or unsaturated $C_{12-20}$ alkyl amine base or a saturated or unsaturated $C_{12-20}$ alkyl polyamine base, or mixtures thereof.

1.11 Any of the preceding compositions, wherein the amine base is a myristyl, palmityl, linoleyl, oleyl, or stearyl amine or polyamine, or combinations thereof.

1.12 Any of the preceding compositions, wherein the amine base is a polyamine (e.g., a monoamine base, a diamine base and/or a triamine base).

1.13 Any of the preceding compositions, wherein the amine base is a monoamine base.

1.14 Any of the preceding compositions, wherein the amine base is a diamine base.

1.15 Any of the preceding compositions, wherein the amine base is a triamine base.

1.16 Any of the preceding compositions, wherein the amine base comprises one or more of N'-octadecylt-rimethylendiamine-N,N,N'-tris(2-ethanol), and/or N-octadeca-9-enylamine.

1.17 Any of the preceding compositions, wherein the amine base is N'-octadecyltrimethylendiamine-N,N,N'-tris(2-ethanol).

1.18 Any of the preceding compositions, wherein the amine base is N-octadeca-9-enylamine.

1.19 Any of the preceding compositions, wherein the amine base and fluoride ion source form amine fluoride in situ.

1.20 Any of the preceding compositions, further comprising an acid.

1.21 The preceding composition, wherein the acid is an organic acid (e.g., lactic acid, citric acid, tartaric acid, fumaric acid, malic acid), phosphoric acid or hydrochloric acid.

1.22 The preceding composition, wherein the organic acid is an aliphatic di- or tri-carboxylic acid in free or salt form.

1.23 Any of the preceding compositions, further comprising malic acid.

1.24 Any of the preceding compositions, further comprising hydrochloric acid.

1.25 Any of the preceding compositions, further comprising phosphoric acid.

1.26 Any of the preceding compositions, wherein the acid is not hydrofluoric acid.

1.27 Any of the preceding compositions, wherein the composition is substantially free of hydrofluoric acid (e.g., less than 0.001 wt. % hydrofluoric acid).

1.28 Any of the preceding compositions, wherein the amine base, fluoride ion source, and the acid form amine fluoride in situ.

1.29 Any of the preceding compositions, wherein the fluoride source is selected from one or more of sodium fluoride, potassium fluoride, sodium fluorosilicate, ammonium fluorosilicate, amine fluoride, ammonium fluoride, and combinations thereof.

1.30 Any of the preceding compositions, wherein the fluoride is sodium fluoride.

1.31 Any of the preceding compositions, wherein the composition comprises less than 0.01 wt. % stannous fluoride.

1.32 Any of the preceding compositions, wherein the composition comprises less than 0.001 wt. % stannous fluoride.

1.33 Composition 1.19 or 1.28, wherein the amine fluoride formed is one or more of N'-octadecyltrimethyl-endiamine-N,N,N'-tris(2-ethanol)-dihydrofluoride (olaflur) or N-octadeca-9-enylamine hydrofluoride (dectaflur).

1.34 Composition 1.19 or 1.28, wherein the amine fluoride formed is N'-octadecyltrimethylendiamine-N,N, N'-tris(2-ethanol)-dihydrofluoride (olaflur).

1.35 Composition 1.19 or 1.28, wherein the amine fluoride formed is N-octadeca-9-enylamine hydrofluoride (dectaflur).

1.36 Any of the preceding compositions, wherein the zinc source is zinc lactate.

1.37 Any of the preceding compositions, wherein the zinc source is zinc citrate.

1.38 Any of the preceding compositions, wherein the amine base is present in an amount of about 0.01 wt. % to about 5 wt. %, about 0.01 wt. % to about 3 wt. %, or about 0.1 wt. % to about 1 wt. % based on the total weight of the composition.

1.39 Any of the preceding compositions, wherein the amine base is present in an amount of about 0.5 wt. % to about 2.5 wt. %, about 1 wt. % to about 2 wt. %, about 1.2 wt. % to about 1.4 wt. %, or about 1.3 wt. %, based on the total weight of the composition.

1.40 Any of the preceding compositions, wherein the amine base is present in an amount of about 0.1 wt. % to about 0.5 wt. %, or about 0.15 wt. % to about 0.25 wt. %, based on the total weight of the composition.

1.41 The preceding composition wherein the fluoride ion source is present in an amount of 0.005 wt. % to 2.5 wt. % (e.g., about 0.025 wt. % to about 0.145 wt. %), about 0.1 wt. % to about 0.5 wt. %, or about 0.01 wt. % to about 0.03 wt. %, based on the total weight of the composition.

1.42 Any of the preceding compositions, wherein the total fluoride content of the composition is in an amount of from 50 to 25,000 ppm (e.g., 750-7000 ppm, e.g., 1000-5500 ppm, e.g., about 250 ppm, 500 ppm, 1000 ppm, 1100 ppm, 1400 ppm, 1450 ppm, 2800 ppm, 5000 ppm, or 25000 ppm).

1.43 Any of the preceding compositions, wherein the zinc source is present in an amount of about 0.1 wt. % to about 2.5 wt. %, e.g., about 0.5 wt. % or about 2.0 wt. %, based on the total weight of the composition.

1.44 Any of the preceding compositions, wherein the zinc source is present in an amount of about 0.1 wt. % to about 0.2 wt. %, e.g., about 0.17 wt. % to about 0.18 wt. %, based on the total weight of the composition.

1.45 Any of the preceding compositions, wherein the zinc source is zinc lactate present in an amount of about 0.5 wt. %, based on the total weight of the composition.

1.46 Any of the preceding compositions, wherein the zinc source is zinc lactate present in an amount of about 0.1 wt. % to about 0.25 wt. %, or 0.2 wt. %, based on the total weight of the composition.

1.47 Any of the preceding compositions, wherein the zinc source is zinc citrate present in an amount of about 2.0 wt. %, based on the total weight of the composition.

1.48 Any of the preceding compositions, further comprising polyvinyl pyrrolidone in an amount of about 0.1 wt. % to about 1.00 wt. %, based on the total weight of the composition.

1.49 Any of the preceding compositions, comprising an acid (e.g., hydrochloric acid) in an amount of about 0.1 wt. % to about 1.0 wt. % (e.g., about 0.7 wt. % to about 0.9 wt. %), based on the total weight of the composition.

1.50 Any of the preceding compositions, comprising malic acid in an amount of about 0.03 wt. % to about 0.07 wt. %, based on the total weight of the composition.

1.51 Any of the preceding compositions, comprising a cellulose derivative (e.g., hydroxyethyl cellulose) in an amount of about 1 wt. % to about 2 wt. %, based on the total weight of the composition.

1.52 Any of the preceding compositions, further comprising a basic amino acid (e.g., arginine) present in an amount corresponding to 1% to 15%, e.g., 3 wt. % to 10 wt. % of the total composition weight, about e.g., 1.5%, 4%, 5%, or 8%, wherein the weight of the basic amino acid is calculated as free form.

1.53 Any of preceding compositions, wherein the composition is ethanol-free.

1.54 Any of the preceding compositions, wherein the pH is below 7, e.g., a pH of about 3-6, e.g., a pH of about 4-5.

1.55 Any of the preceding compositions, further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, disodium hydrogenorthophoshpate, monosodium phosphate, pentapotassium triphosphate and mixtures of any of two or more of these, e.g., in an amount of 0.01-20%, e.g., 0.1-8%, e.g., e.g., 0.1 to 5%, e.g., 0.3 to 2%, e.g., 0.3 to 1%, e.g., about 0.01%, about 0.1%, about 0.5%, about 1%, about 2%, about 5%, about 6%, by weight of the composition.

1.56 The preceding composition, wherein the polyphosphate is tetrasodium pyrophosphate.

1.57 The preceding composition, wherein the tetrasodium pyrophosphate is from 0.1-1.0 wt. % (e.g., about 0.5 wt. %).

1.58 Any of the preceding compositions, further comprising an abrasive or particulate (e.g., silica).

1.59 Any of the preceding compositions, further comprising a nonionic surfactant, wherein the nonionic surfactant is in an amount of from 0.5-5%, e.g., 1-2%, selected from poloxamers (e.g., poloxamer 407), polysorbates (e.g., polysorbate 20), polyoxyl hydrogenated castor oil (e.g., polyoxyl 40 hydrogenated castor oil), polyglyceryl 4-caprate, and mixtures thereof.

1.60 The preceding composition, wherein the poloxamer nonionic surfactant has a polyoxypropylene molecular mass of from 3000 to 5000 g/mol and a polyoxyethylene content of from 60 to 80 mol %, e.g., the poloxamer nonionic surfactant comprises poloxamer 407.

1.61 Any of the preceding compositions, further comprising a humectant selected from glycerin, sorbitol, xylitol, propylene glycol in an amount of about 10-70 wt. % based on the total weight of the composition.

1.62 Any of the preceding compositions, comprising a humectant selected from glycerin and sorbitol.

1.63 Any of the preceding compositions, further comprising a flavoring, fragrance and/or coloring agent.

1.64 Any of the preceding compositions, comprising one or more flavoring agents selected from saccharin and sucralose (e.g., saccharin in an amount of about 0.02 wt. % and sucralose in an amount of about 0.007 wt. % to about 0.01 wt. %).

1.65 The preceding composition, further comprising glycerin in an amount of about 2.0 wt. % to about 3.5 wt. %, based on the total weight of the composition.

1.66 Any of the preceding compositions, further comprising a thickening agent selected from the group consisting of carboxyvinyl polymers, hydroxyethyl cellulose and water-soluble salts of cellulose ethers (e.g., sodium carboxymethyl cellulose and sodium carboxymethyl hydroxyethyl cellulose).

1.67 Any of the preceding compositions, further comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, honokiol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC), phenolic antiseptics, hexetidine, octenidine, sanguinarine, povidone iodine, delmopinol, salifluor, sanguinarine, propolis and oxygenating agents (e.g., buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.

1.68 Any of the preceding compositions, further comprising an antioxidant, e.g., selected from the group consisting of Co-enzyme Q10, PQQ, Vitamin C, Vitamin E, Vitamin A, BHT, anethole-dithiothione, and mixtures thereof.

1.69 Any of the preceding compositions, further comprising a whitening agent selected from the group consisting of metal chlorites, perborates, percarbonates, peroxyacids, hypochlorites, and combinations thereof.

1.70 Any of the preceding compositions, further comprising an agent that interferes with or prevents bacterial attachment, e.g. ethyl lauroyl arginiate (ELA) or chitosan.

1.71 Any of the preceding compositions, wherein the oral composition may be any of the following oral compositions selected from the group consisting of: a toothpaste or a dentifrice, a mouthwash or a mouth rinse, a topical oral gel, sprays, powders, strips, floss and a denture cleanser.

1.72 Any of the preceding compositions, wherein the composition is in the form of a cleanser such as a liquid hand soap formulation, body wash, or skin cleanser, or a home care formulation, e.g., a hard surface cleanser such as a dish soap, sunscreen, a makeup remover, or a topical disinfectant.

1.73 Any of the preceding compositions, for use in the treatment of periodontitis and/or gingivitis.

A composition obtained or obtainable by combining the ingredients as set forth in any of the preceding compositions.

In another embodiment, the present disclosure encompasses a method to improve oral health comprising applying an effective amount of the oral composition of any of the embodiments set forth above to the oral cavity of a subject in need thereof, e.g., a method to i. reduce or inhibit formation of dental caries, ii. reduce, repair or inhibit early enamel lesions, e.g., as detected by quantitative light-induced fluorescence (QLF) or electrical caries measurement (ECM), iii. reduce or inhibit demineralization and promote remineralization of the teeth, iv. reduce hypersensitivity of the teeth, v. reduce or inhibit gingivitis, vi. promote healing of sores or cuts in the mouth, vii. inhibit microbial biofilm formation in the oral cavity, viii. raise and/or maintain plaque pH at levels of at least pH 5.5 following sugar challenge, ix. reduce plaque accumulation, x. treat dry mouth, xi. enhance systemic health, including cardiovascular health, e.g., by reducing potential for systemic infection via the oral tissues, xii. whiten teeth, xiii. reduce erosion of the teeth, xiv. immunize (or protect) the teeth against cariogenic bacteria and their effects, and/or xv. clean the teeth and oral cavity.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., each of which are incorporated herein by reference. Representative fluoride ion sources used with the present disclosure (e.g., Composition 1.0 et seq.) include, but are not limited to, sodium fluoride, potassium fluoride, sodium fluorosilicate, ammonium fluorosilicate, amine fluoride, ammonium fluoride, and combinations thereof. In certain embodiments the fluoride ion source includes sodium fluoride. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

Surfactants

In another embodiment, cationic surfactants useful in the present disclosure can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants of Composition 1.0, et seq., that can be used in the compositions of the disclosure can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the disclosure comprises a nonionic surfactant selected from poloxamers (e.g., poloxamer 407), polysorbates (e.g., polysorbate 20), polyoxyl hydrogenated castor oils (e.g., polyoxyl 40 hydrogenated castor oil), betaines (such as cocamidopropylbetaine), and mixtures thereof.

Illustrative amphoteric surfactants of Composition 1.0, et seq., that can be used in the compositions of the disclosure include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials.

The surfactant or mixtures of compatible surfactants can be present in the compositions of the present disclosure in 0.1% to 5%, in another embodiment 0.3% to 3% and in another embodiment 0.5% to 2% by weight of the total composition.

Flavoring Agents

The oral care compositions of the disclosure may also include a flavoring agent. Flavoring agents which are used in the practice of the present disclosure include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 1.7% by weight.

Chelating and Anti-Calculus Agents

The oral care compositions of the disclosure also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present disclosure are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide least 0.1 wt. % pyrophosphate ions, e.g., 0.1 to 3 wt. 5, e.g., 0.1 to 2 wt. %, e.g., 0.1 to 1 wt. %, e.g., 0.2 to 0.5 wt. %. The pyrophosphates also contribute to preservation of the compositions by lowering water activity.

Polymers

The oral care compositions of the disclosure also optionally include one or more polymers, such as polyethylene glycols, polyvinyl methyl ether maleic acid copolymers, polysaccharides (e.g., cellulose derivatives, for example carboxymethyl cellulose). Acidic polymers, for example polyacrylate gels, may be provided in the form of their free acids or partially or fully neutralized water-soluble alkali metals (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, hydroxyethyl cellulose and water-soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Abrasives

In certain embodiments the disclosure may comprise additional silica abrasives, sodium metaphosphate, potassium metaphosphate, aluminum silicate, calcined alumina, bentonite or other siliceous materials, or combinations thereof. Any silica suitable for oral care compositions may be used, such as precipitated silicas or silica gels. For example, synthetic amorphous silica. Silica may also be available as a thickening agent, e.g., particle silica. For example, the silica can also be small particle silica (e.g., Sorbosil AC43 from PQ Corporation, Warrington, United Kingdom).

Water

Water is present in the oral compositions of the disclosure. Water, employed in the preparation of commercial oral compositions should be deionized and free of organic impurities. Water commonly makes up the balance of the compositions and includes 5% to 99%, e.g., 10% to 20%, e.g., 25-35%, by weight of the oral compositions. This amount of water includes the free water which is added plus that amount which is introduced with other materials such as with sorbitol or silica or any components of the disclosure. The Karl Fischer method is a one measure of calculating free water.

Humectants

Within certain embodiments of the oral compositions, it is also desirable to incorporate a humectant to reduce evaporation and also contribute towards preservation by lowering water activity. Certain humectants can also impart desirable sweetness or flavor to the compositions. The humectant, on a pure humectant basis, generally includes 1% to 70% in one embodiment or 30% to 65% in another embodiment by weight of the composition.

Suitable humectants include edible polyhydric alcohols such as glycerin, sorbitol, xylitol, propylene glycol as well as other polyols and mixtures of these humectants. Mixtures of glycerin and sorbitol may be used in certain embodiments as the humectant component of the compositions herein.

pH Adjusting Agents

In some embodiments, the compositions of the present disclosure contain a buffering agent. Examples of buffering agents include anhydrous carbonates such as sodium carbonate, sesquicarbonates, bicarbonates such as sodium bicarbonate, silicates, bisulfates, phosphates (e.g., monopotassium phosphate, dipotassium phosphate, tribasic sodium phosphate, sodium tripolyphosphate, phosphoric acid), citrates (e.g. citric acid, trisodium citrate dehydrate), pyrophosphates (sodium and potassium salts) and combinations thereof. The amount of buffering agent is sufficient to provide a pH of about 3 to about 9, preferable about 4 to about 5, when the composition is dissolved in water, a mouth rinse base, or a toothpaste base. Typical amounts of buffering agent are about 5% to about 35%, in one embodiment about 10% to about 30%, in another embodiment about 15% to about 25%, by weight of the total composition.

The present disclosure in its method aspect involves applying to the oral cavity a safe and effective amount of the compositions described herein.

The compositions and methods according to the disclosure (e.g., Composition 1.0 et seq) can be incorporated into oral compositions for the care of the mouth and teeth such as toothpastes, transparent pastes, gels, mouthwashes, mouth rinses, sprays, toothpaste powders, tablets and chewing gum.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present disclosure. The examples are given solely for illustration and are not to be construed as limitations of this disclosure as many variations are possible without departing from the spirit and scope thereof. Various modifications of the disclosure in addition to those shown and described herein should be apparent to those skilled in the art and are intended to fall within the appended claims.

EXAMPLES

Example 1: Model Toothpaste Formulations

Toothpaste formulations were prepared according to the following:

TABLE 1

| Toothpaste formulations according to the present disclosure | | | |
|---|---|---|---|
| | Formulation 1 | Formulation 2 | Formulation 3 |
| Surfactants | 5.5 | 5.5 | 5.5 |
| Polymers | 1.6 | 1.6 | 1.6 |
| Amine base (bovine tallow-derived) | 1.38 | — | — |
| Hydrochloric acid | 0.79 | 0.88 | 0.89 |
| Sodium saccharin | 0.39 | 0.39 | 0.39 |

TABLE 1-continued

| Toothpaste formulations according to the present disclosure | | | |
|---|---|---|---|
| | Formulation 1 | Formulation 2 | Formulation 3 |
| Glycerin | 40 | 40 | 40 |
| Amorphous silica | 19 | 19 | 19 |
| Thickening silica | 2.7 | 2.7 | 2.7 |
| Zinc lactate | 0.5 | 0.5 | — |
| Zinc citrate | — | — | 2.0 |
| Sodium fluoride | 0.31 | 0.31 | 0.31 |
| Amine base (Plant-derived) | — | 1.38 | 1.38 |
| Fragrants and colorants | 1.6 | 1.6 | 1.6 |
| water | 26.24 | 26.15 | 24.64 |

Formulations 1-3 were subjected to accelerated aging conditions in order to test shelf stability. Results are summarized below in Table 2.

TABLE 2

| Stability of toothpaste formulations | | | | | |
|---|---|---|---|---|---|
| | Time | Condition | Ionic Fluoride | Viscosity | Appearance |
| Formulation 1 | Initial | 30° C./65% rel. humidity | 1394 ppm | 370 pas | Pass |
| | 3 Months | 30° C./65% rel. humidity | 1356 ppm | 358 pas | Pass |
| | 3 Months | 40° C./75% rel. humidity | 1321 ppm | 349 pas | Pass |
| Formulation 2 | Initial | 30° C./65% rel. humidity | 1386 ppm | 357 pas | Pass |
| | 3 Months | 30° C./65% rel. humidity | 1372 ppm | 358 pas | Pass |
| | 3 Months | 40° C./75% rel. humidity | 1330 ppm | 361 pas | Pass |
| Formulation 3 | Initial | 30° C./65% rel. humidity | 1406 ppm | 499 pas | Pass |
| | 3 Months | 30° C./65% rel. humidity | 1375 ppm | 445 pas | Pass |
| | 3 Months | 40° C./75% rel. humidity | 1341 ppm | 301 pas | Pass |

As shown above, each of the formulations showed a high level of stability, even under accelerated aging conditions.

A number of control toothpaste formulations were created as comparators to Formulations 1-3, and are summarized in Table 2.

TABLE 3

| Control toothpaste formulations | | |
|---|---|---|
| | Comparator Formulation 1 (wt. %) | Comparator Formulation 2 (wt. %) |
| Sorbitol | 30-40 | 30-40 |
| Glycerin | — | — |
| Silica | 15-25 | 15-25 |
| Sodium fluoride | — | 0.2-0.4 |
| Surfactants | 1-5 | 1-5 |
| Polymers | 3-5 | 3-5 |
| Sodium gluconate | 1-2 | 1-2 |
| Amine base | 1.38 | — |
| Hydrochloric acid | 0.46 | 0.1-1 |
| Hydrofluoric acid | 0.09 | — |
| Stannous fluoride | 0.44 | — |

TABLE 3-continued

| | Comparator Formulation 1 (wt. %) | Comparator Formulation 2 (wt. %) |
|---|---|---|
| Control toothpaste formulations | | |
| Potassium hydroxide | 0.1-1 | — |
| Formula OC AI 590-4 | 5-10 | — |
| Fragrants, sweeteners and colorants | 1-3 | 1-3 |
| Water | q.s. | q.s. |

Example 2: In Vitro Antibacterial Testing of Toothpaste Formulations

Preparations were created to test the in vitro antibacterial activity of various toothpaste formulations according to the present disclosure. McBain media was diluted and supplemented with a 1:1000 dilution of hemin and menadione. The media was then inoculated at a concentration of 2 mL per 40 mL of media. HAP discs were placed inside the plates as a substrate for biofilm growth, and were allowed to incubate for 60 hours. 1.5 mL media was refilled every 12 hours.

1.5 mL of the test formulations were added to each plate. The HAP disc was treated for 2 minutes and incubated in an orbital shaker at 90 rpm. Bacterial viability was determined by ATP fluorescence. The results are summarized below in Table 3:

TABLE 4

| Composition | Fluorescence counts |
|---|---|
| Antibacterial Activity | |
| Formulation 1 | 29712 |
| Formulation 2 | 33862 |
| Formulation 3 | 42957 |
| Comparator Formulation 1 | 40756 |
| Comparator Formulation 2 | 155913 |

As shown above, the compositions containing zinc lactate or zinc citrate with an amine base and sodium fluoride performed at least as well as or better than the Comparator Formulation 1, which did not contain any zinc compounds. Additionally, each of compositions 1-3 performed far better than Comparator Formulation 2, which contained sodium fluoride without an amine base or a zinc compound. These results show that oral care compositions containing an amine base, sodium fluoride and a zinc compound provide a surprising boost in the antibacterial efficacy of the composition.

Example 3: In Vitro Antibacterial Testing of Mouthwash Formulations

A mouthrinse formulation according to the present disclosure was prepared as summarized in Table 5.

TABLE 5

| | Formulation 4 | Formulation 5 | Formulation 6 |
|---|---|---|---|
| Mouthrinse compositions | | | |
| Xylitol | 1.5 | 2.5 | 2.5 |
| Polyvinyl pyrrolidone | 0.2 | 0.8 | 0.8 |
| Castor oil | 0.25 | — | 0.25 |

TABLE 5-continued

| | Formulation 4 | Formulation 5 | Formulation 6 |
|---|---|---|---|
| Mouthrinse compositions | | | |
| Zinc lactate | 0.2 | 0.2 | 0.2 |
| Amine base | 0.16 | 0.15 | 0.16 |
| Hydrofluoric acid | 0.03 | 0.03 | 0.03 |
| Polyglyceryl 4-caprate | — | 0.25 | — |
| Sodium fluoride | 0.03 | 0.03 | 0.03 |
| Glycerin | — | 2.0 | 2.0 |
| Flavorants, sweeteners and colorants | 0.17 | 0.16 | 0.16 |
| water | q.s | q.s. | q.s. |

The above compositions were analyzed in a short-term kill test against several comparator compositions. The comparator compositions were prepared according to the summary in Table 6.

TABLE 6

| | Comparator Formulation 3 | Comparator Formulation 4 |
|---|---|---|
| Comparator mouthrinse compositions | | |
| Xylitol | 0.1-1 | 0.1-1 |
| Polyvinyl pyrrolidone | 0.1-1 | 0.1-1 |
| Castor oil | 0.1-1 | 0.1-1 |
| Amine base | 0.16 | — |
| Stannous fluoride | 0.05 | — |
| Sodium saccharin | 0.01-0.1 | 0.01-0.1 |
| Hydrofluoric acid | 0.01-0.1 | 0.01-0.1 |
| Flavorants, sweeteners and colorants | 0.1-1 | 0.1-1 |
| water | q.s | q.s |

In the short interval kill test, whole saliva is mixed 1:1 with mouthwash for 1 min contact time. The reaction is stopped with a neutralizing broth and samples are serially diluted and plated. Data are reported as a reduction in the log (colony forming units) relative to a buffer-treated negative control. Results are summarized below.

TABLE 7

| Composition | Log reduction in CFUs |
|---|---|
| SIKT test results | |
| Formulation 4 | 4.05 |
| Comparator Formulation 3 | 2.91 |
| Comparator Formulation 4 | 0.27 |

As these results show, Formulation 4, containing zinc lactate and amine fluoride, performed markedly better than Comparator Formulation 3 (containing amine fluoride and stannous fluoride actives), giving over 1 log greater reduction than other samples.

A further study was carried out using an in vitro plaque glycolysis model based on the PGRM clinical study found in the tentative US FDA monograph on plaque and gingivitis. This model uses saliva derived biofilms, instead of plaque and monitors pH changes following treatment with test mouthwashes as a measure of a formula's ability to limit the metabolic activity of biofilms.

Saliva-derived biofilms were cultured on attached hydroxyapatite discs in McBain media supplemented with 0.4% sucrose at 37° C. under an environment containing 5% $CO_2$. The biofilm was cultured for 48 hours with the media replaced after 24 hours of initial outgrowth. The resulting biofilms were treated with undiluted mouthwash rinse for 5 min and rinsed by dipping for 30 seconds in sterile deionized water for two consecutive times. Each treatment was performed in four replicates. All treated biofilms were then incubated in 0.3% TSB supplemented with 0.5% sucrose, pH 7.2 for 6.5 hrs. The final pH is measured for each biofilm sample and the pH change (Initial pH-Final pH) is calculated for each sample.

TABLE 8

| pH changes following exposure to test formulations | |
| --- | --- |
| Composition | Change in pH |
| Formulation 4 | 1.75 |
| Comparator Formulation 3 | 1.69 |
| Comparator Formulation 4 | 2.7 |
| Untreated | 2.75 |

Results from the in-vitro plaque glycolysis study indicate that both the Comparator Formulations 5 and 6 containing Amine fluoride and stannous fluoride showed a significant reduction in acid production in comparison to the placebo treatment and positive control. Both of these mouthwashes performed in parity, suggesting that the efficacy of the formulation is not affected over time. Formulation 4 containing amine fluoride and zinc lactate also showed a significant reduction in bacterial activity in comparison to the placebo treatment and positive control. Without being bound by theory, it is believed that the resulting antibacterial activity of Formulation 4 as well as Comparator Formulations 5 and 6 is likely due to the presence of amine fluoride in addition to the metal ions.

A further study was conducted using an aerobic biofilm model, in which saliva-derived biofilms are grown on HAP discs suspended vertically. Biofilms are grown in a complex medium (SHI medium) chosen because it has been shown to give a high degree of diversity in saliva-derived biofilms. Biofilms are treated twice per day with 1.5 mL of test mouthwash for 30 seconds each treatment. Following 5 days of growth, biofilms are harvested and total biomass (optical density at 610 nm, i.e., $OD_{610}$) and metabolic activity, as measured by ATP activity, are quantified.

TABLE 9

| Reduction of bacteria by $OD_{610}$ | |
| --- | --- |
| Composition | Reduction of bacteria (%) |
| Formulation 4 | 51.39 |
| Comparator Formulation 3 | 45.78 |
| Comparator Formulation 4 | 5.13 |

TABLE 10

| Reduction of bacteria by ATP fluorescence detection | |
| --- | --- |
| Composition | Reduction of bacteria (%) |
| Formulation 4 | 89.90 |
| Comparator Formulation 3 | 77.15 |
| Comparator Formulation 4 | 2.91 |

A study test was conducted to test the stability of the compositions after exposing the composition to air (i.e., after first use). As shown below, while Comparator Formulation 3 still shows antibacterial effect over the test period, the efficacy decreases substantially over time. On the other hand, Formulation 4 does not show this same trend, indicating that the active ingredients in these formulations are more stable and remain active over time.

TABLE 11

| Reduction of bacteria by $OD_{610}$ over time | | |
| --- | --- | --- |
| | Time | Reduction of bacteria (%) |
| Formulation 4 | Initial | 54 |
| | 1 week | 50 |
| | 3 weeks | 48 |
| Comparator Formulation 3 | Initial | 68 |
| | 1 week | 42 |
| | 3 weeks | 28 |
| Comparator Formulation 4 | Initial | 12 |
| | 1 week | 0 |
| | 3 weeks | 2 |

While the present disclosure has been described with reference to embodiments, it will be understood by those skilled in the art that various modifications and variations may be made therein without departing from the scope of the present disclosure as defined by the appended claims.

The invention claimed is:

1. An oral care composition comprising:
   an amine base,
   sodium fluoride in an amount of about 0.1 wt. % to about 0.5 wt. %,
   zinc lactate in an amount of about 0.2 wt. % to about 0.5 wt. %,
   a surfactant,
   a humectant, and
   hydrochloric acid,
   wherein the composition comprises less than 0.001 wt. % stannous fluoride, the amine base, sodium fluoride, and hydrochloric acid form amine fluoride *in situ*, and the wt. percents are based on the total weight of the composition.

2. The composition according to claim 1, wherein the oral care composition is in the form of a toothpaste, a dentifrice, a mouthwash, a mouth rinse, a topical oral gel, a denture cleanser, or a dental spray.

\*  \*  \*  \*  \*